United States Patent
Silverman et al.

(10) Patent No.: US 7,318,801 B2
(45) Date of Patent: *Jan. 15, 2008

(54) METHOD FOR TREATING FECAL INCONTINENCE

(75) Inventors: David E. Silverman, Palo Alto, CA (US); Alan Stein, Moss Beach, CA (US)

(73) Assignee: Scimed Life Systems, Inc., Maple Grove, MN (US)

(*) Notice: Subject to any disclaimer, the term of this patent is extended or adjusted under 35 U.S.C. 154(b) by 707 days.

This patent is subject to a terminal disclaimer.

(21) Appl. No.: 10/621,191

(22) Filed: Jul. 15, 2003

(65) Prior Publication Data

US 2004/0010182 A1 Jan. 15, 2004

Related U.S. Application Data

(63) Continuation of application No. 09/882,522, filed on Jun. 15, 2001, now Pat. No. 6,595,910, which is a continuation-in-part of application No. 09/286,245, filed on Apr. 5, 1999, now Pat. No. 6,251,063, which is a continuation-in-part of application No. 09/232,056, filed on Jan. 15, 1999, now Pat. No. 6,238,335.

(60) Provisional application No. 60/111,884, filed on Dec. 11, 1998.

(51) Int. Cl.
*A61F 2/02* (2006.01)
(52) U.S. Cl. ...................................... 600/30
(58) Field of Classification Search ........ 128/DIG. 25, 128/897, 898; 600/39–41, 127, 129, 104; 606/1; 604/13, 164.06, 170.03, 17, 49; 623/7, 623/8; 424/502
See application file for complete search history.

(56) References Cited

U.S. PATENT DOCUMENTS

| | | |
|---|---|---|
| 3,094,122 A | 6/1963 | Gauthier et al. |
| 3,204,634 A | 9/1965 | Koehn |
| 4,351,333 A | 9/1982 | Lazarus et al. |
| 4,424,208 A | 1/1984 | Wallace et al. |
| 4,582,640 A | 4/1986 | Smestad et al. |
| 4,773,393 A | 9/1988 | Haber et al. |
| 4,803,075 A | 2/1989 | Wallace et al. |

(Continued)

FOREIGN PATENT DOCUMENTS

AU    A-34223/95    5/1996

(Continued)

OTHER PUBLICATIONS

Donahue, P. et al., "Endoscopic Sclerosis Of The Gastric Cardia For Prevention Of Experimental Gastroesophageal Reflux" (1990) Gastrointestinal Endoscopy, pp. 253-256.

(Continued)

*Primary Examiner*—Samuel G. Gilbert
(74) *Attorney, Agent, or Firm*—Dorsey & Whitney LLP

(57) ABSTRACT

A method for treating fecal incontinence in a body of a mammal having a rectum formed by a rectal wall extending to an anus wherein the rectal wall includes a sphincter muscle surrounding the anus. At least one nonaqueous solution is introduced into the rectal wall in the vicinity of the anus. A nonbiodegradable solid is formed in the rectal wall from the at least one nonaqueous solution.

18 Claims, 2 Drawing Sheets

U.S. PATENT DOCUMENTS

| | | | |
|---|---|---|---|
| 4,837,285 A | 6/1989 | Berg et al. | |
| 5,007,940 A | 4/1991 | Berg | |
| 5,067,965 A | 11/1991 | Ersek et al. | |
| 5,116,387 A | 5/1992 | Berg | |
| 5,158,573 A | 10/1992 | Berg | |
| 5,204,382 A | 4/1993 | Wallace et al. | |
| 5,258,028 A | 11/1993 | Ersek et al. | |
| 5,301,682 A | 4/1994 | Debbas | |
| 5,336,263 A | 8/1994 | Ersek et al. | |
| 5,451,406 A | 9/1995 | Lawin et al. | |
| 5,480,644 A | 1/1996 | Freed | |
| 5,490,984 A | 2/1996 | Freed | |
| 5,580,568 A | 12/1996 | Greff et al. | |
| 5,667,767 A | 9/1997 | Greff et al. | |
| 5,695,480 A | 12/1997 | Evans et al. | |
| 5,702,361 A | 12/1997 | Evans et al. | |
| 5,755,658 A | 5/1998 | Wallace et al. | |
| 5,785,642 A | 7/1998 | Wallace et al. | |
| 5,792,478 A | 8/1998 | Lawin et al. | |
| 5,830,178 A | 11/1998 | Jones et al. | |
| 5,855,615 A | 1/1999 | Bley et al. | |
| 6,096,021 A | 8/2000 | Helm et al. | |
| 6,251,063 B1 | 6/2001 | Silverman et al. | |
| 6,251,064 B1 | 6/2001 | Silverman et al. | |
| 6,335,028 B1 | 1/2002 | Vogel et al. | |
| 6,533,717 B2 * | 3/2003 | Silverman et al. | 600/29 |
| 6,595,910 B2 * | 7/2003 | Silverman et al. | 600/29 |
| 2001/0018548 A1 | 8/2001 | Silverman et al. | |

FOREIGN PATENT DOCUMENTS

| | | |
|---|---|---|
| WO | WO 97/19643 | 6/1997 |
| WO | WO 97/45131 | 12/1997 |
| WO | WO 98/01088 | 1/1998 |
| WO | WO 98/17200 | 4/1998 |
| WO | WO 98/17201 | 4/1998 |

OTHER PUBLICATIONS

Klingman, R.R. et al., "The Current Management of Gastroesophageal Reflux", (1991), *Adv. Surg.*, vol. 24, pp. 259-291.

Malizia, A. et al., "Migration and Granulomatous Reaction After Periurethral injection of Polytef (Teflon)", (Jun. 1984), *JAMA*, vol. 251, No. 24, pp. 3277-3281.

O'Connor, K.W. et al., "Endoscopic placement of collagen at the lower esophageal sphincter to inhibit gastroesophageal reflux: a pilot study of 10 medically intractable patients", (1988), *Gastrointestinal Endoscopy*, vol. 34, No. 2, pp. 106-112.

O'Connor, K. W. et al., "An experimental endoscopic technique for reversing gastroesophageal reflux in dogs by injecting inert material in the distal esophagus", (1984) Gatrointestinal Endoscopy, vol. 30, No. 5, pp. 275-280.

Ortiz, A. et al., "Conservative treatment versus antireflux surgery in Barrett's oesophagus: long-term results of a prospective study", (1996), *Brit. Jnl. of Surg.*, vol. 83, 274-278.

Politano, V.A., et al., "Periurethral Teflon Injection for Urinary Incontinence", (Feb. 1974) *Jnl. Urology*, vol. 111, pp. 180-183.

Schulman, C.C. et al., "Endoscopic injections of Teflon to treat urinary incontinence in women", (Jan. 21, 1984) *BMJ*, vol. 228, p. 192.

Shafik, A., "Intraesophageal Polytef injection for the treatment of reflux esophagitis", (1996), *Surgical Endoscopy*, pp. 329-331.

Walker, R.D. et al., "Injectable Bioglass as a Potential Substitute for Injectable Polytetrafluoroethylene", (Aug. 1992), *J. Urol.*, vol. 148, pp. 645-647.

* cited by examiner

METHOD FOR TREATING FECAL INCONTINENCE

This application is a continuation application of U.S. utility patent application Ser. No. 09/882,522 filed Jun. 15, 2001, now U.S. Pat. No. 6,595,910, which is a continuation-in-part of U.S. patent application Ser. No. 09/286,245 filed Apr. 5, 1999, now U.S. Pat. No. 6,251,063, which is a continuation-in-part of U.S. patent application Ser. No. 09/232,056 filed Jan. 15, 1999, now U.S. Pat. No. 6,238,335, and claims the benefit of U.S. provisional patent application Ser. No. 60/111,884 filed Dec. 11, 1998, the entire contents of each of which are incorporated herein by this reference.

This invention pertains to the treatment of the gastrointestinal tract and, more particularly, to the treatment of fecal incontinence.

Fecal incontinence, which is most common in the elderly, is the loss of voluntary control to retain stool in the rectum. In most cases, fecal incontinence is the result of an impaired involuntary internal anal sphincter. The internal sphincter may be incompetent due to laxity or discontinuity. Discontinuity, or disruption of the internal anal sphincter, can be caused by a number of different muscle injuries.

In most patients, fecal incontinence is initially treated with conservative measures, such as biofeedback training or alteration of the stool consistency. Biofeedback is successful in approximately two-thirds of patients who retain some degree of rectal sensation and functioning of the external anal sphincter. However, multiple sessions are often necessary, and patients need to be highly motivated. Electronic home biofeedback systems are available and may be helpful as adjuvant therapy.

Several surgical approaches to fecal incontinence have been tried, with varying success, when conservative management has failed. These treatments include sphincter repair, gracilis or gluteus muscle transposition to reconstruct an artificial sphincter and colostomy. The approach that is used depends on the cause of the incontinence and the expertise of the surgeon. For example, biodegradable compounds have been injected or introduced into the anal sphincter to bulk the rectal wall. Unfortunately, such biodegradable compounds are resorbed by the body and thus become ineffective over time.

In general, it is an object of the present invention to provide a minimally invasive method and apparatus for treating fecal incontinence.

Another object of the invention is to provide a method of the above character for treating fecal incontinence in which one or more implants are formed in the rectal wall.

Another object of the invention is to provide a method of the above character for treating fecal incontinence in which one or more implants are formed in the rectal wall in the vicinity of the anal sphincter.

Another object of the invention is to provide a method of the above character in which one or more implants of a nonbiodegradable material are formed in the anal sphincter for reducing the distensibility of the anal sphincter.

Additional objects and features of the invention will appear from the following description from which the preferred embodiments are set forth in detail in conjunction with the accompanying drawings.

In general, a method for treating fecal incontinence in the body of a mammal having a rectum formed by a rectal wall extending to an anus wherein the rectal wall includes a sphincter muscle surrounding the anus is provided. At least one nonaqueous solution is introduced into the rectal wall in the vicinity of the anus. A nonbiodegradable solid is formed in the rectal wall from the nonaqueous solution.

Figures 1, 2, 3, 4:
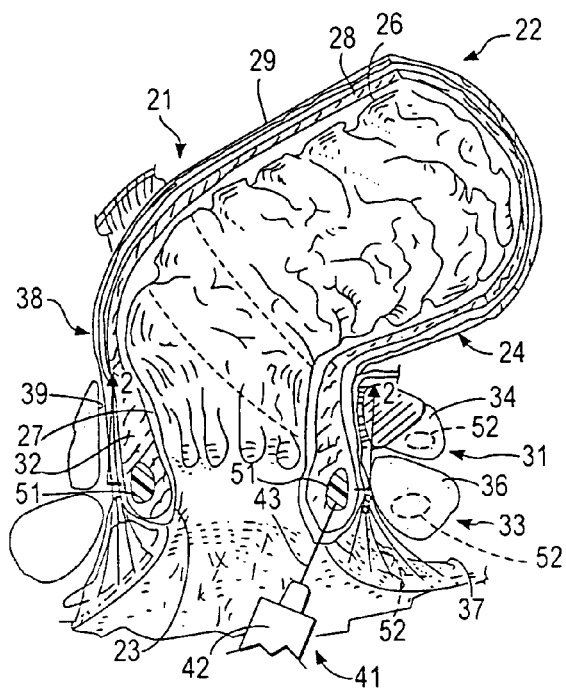
FIG. 1 is a sectional view of a portion of the human body in which a portion of the anal sphincter is being treated by a method of the present invention.
FIG. 2 is a cross-sectional view of a portion of the anal sphincter taken along the line 2-2 of FIG. 1.
FIG. 3 is a sectional view of a portion of the human body similar to FIG. 1 in which a portion of the anal sphincter is being treated by another method of the present invention.
FIG. 4 is a sectional view of a portion of the human body similar to FIG. 1 in which a portion of the anal sphincter is being treated by a further method of the present invention.

As shown in FIG. 1, the gastrointestinal tract includes the rectum 21 and opens to the outside of body 22 at the anus 23. The rectum 21 is formed by a rectal wall 24 substantially centered on a centerline 25 of the rectum (see FIG. 3). The inner layer of the rectal wall 24 is mucosal layer 26, below which is submucosal layer 27. A layer of muscle extends around rectum 21 and also forms part of rectal wall 24. Such muscle layer comprises circular muscle layer 28 extending beneath submucosal layer 27 and longitudinal muscle layer 29 extending beneath circular muscle layer 28. Body 22 further includes the anal sphincter 31 having the sphincter ani internus 32 and the sphincter ani externus 33. Sphincter ani internus 32, an involuntary sphincter, forms the terminus of circular muscle layer 28 at anus 23. Sphincter ani externus 33, a voluntary sphincter, comprises a deep external sphincter 34, the superficial external sphincter 36 and the subcutaneous external sphincter 37. For purposes of this application, the transition between circular muscle 28 and internal sphincter 32 comprises the transition between rectum 21 and anus 23, also known as the anorectal border 38. Also for purposes of this application, rectal wall 24 and thus the wall of the gastrointestinal tract of body 22 includes both sphincter ani internus 32 and sphincter ani externus 33 and thus, the wall of anus 23. Between external and internal sphincters 33 and 32 there exists the potential space known as the inter sphincteric space 39.

In the method for treating fecal incontinence of the present invention, an implantable material such as an implant-forming material or solution is introduced into rectal wall 24 in the vicinity of anal sphincter 31 by any suitable means to augment, bulk or otherwise decrease the distensibility of the anal sphincter 31. The method of the present invention can be performed with any of the apparatus disclosed in U.S. patent application Ser. No. 09/286,245 filed Apr. 5, 1999 and U.S. patent application Ser. No. 09/232,056 filed Jan. 15, 1999. One preferred apparatus for introducing the solution into rectal wall 24 includes a conventional syringe 41 having a barrel 42 filled with the solution. A conventional elongate needle 43 is connected to syringe 41 for delivering the solution from barrel 42 into rectal wall 24. Tubular needle 43 can be of a conventional type and, as such, provided with a single opening at the distal end thereof. Alternatively, needle 43 can be similar to any of the needles described in U.S. patent application Ser. No. 09/232,056 filed Apr. 5, 1999. Syringe 41 is part of the supply assembly of the apparatus of the invention for depositing one or more implants in the rectal area of the patient, and more particularly is a first reservoir containing the implant-forming material. Preferably, the supply assembly further includes a second reservoir containing a solvent, preferably a biocompatible solvent such as dimethyl sulfoxide (DMSO), and a third reservoir containing a suitable aqueous or physiologic solution such as saline.

Although any suitable implant-forming material can be used with the method and/or apparatus of the present invention, one such material is at least one solution which when introduced into the body forms a nonbiodegradable solid. As used herein, a solid means any substance that does not flow perceptibly under moderate stress, has a definite capacity for resisting forces which tend to deform it (such as compression, tension and strain) and under ordinary conditions retains a definite size and shape; such a solid includes, without limitation, spongy and/or porous substances. One such embodiment of the at least one solution is first and second solutions which when combined in the body form the nonbiodegradable solid. Another such embodiment is a nonaqueous solution which can be introduced into the body as a liquid and from which a solid thereafter precipitates. A preferred embodiment of such a nonaqueous or implant-forming solution is a solution of a biocompatible polymer and a biocompatible solvent which can optionally include a contrast agent for facilitating visualization of the solution in the body.

In one embodiment, an implant-forming solution is used that has a composition comprising from about 2.5 to about 8.0 weight percent of a biocompatible polymer, from about 52 to about 87.5 weight percent of a biocompatible solvent and optionally from about 10 to about 40 weight percent of a biocompatible contrast agent having a preferred average particle size of about 10 μm or less. It should be appreciated that any percents stated herein which include a contrast agent would be proportionally adjusted when the contrast agent is not utilized. Any contrast agent is preferably a water insoluble biocompatible contrast agent. The weight percent of the polymer, contrast agent and biocompatible solvent is based on the total weight of the complete composition. In a preferred embodiment, the water insoluble, biocompatible contrast agent is selected from the group consisting of barium sulfate, tantalum powder and tantalum oxide. In still a further preferred embodiment, the biocompatible solvent is dimethylsulfoxide (DMSO), ethanol, ethyl lactate or acetone.

The term "biocompatible polymer" refers to polymers which, in the amounts employed, are non-toxic, chemically inert, and substantially non-immunogenic when used internally in the patient and which are substantially insoluble in physiologic liquids. Suitable biocompatible polymers include, by way of example, cellulose acetates (including cellulose diacetate), ethylene vinyl alcohol copolymers, hydrogels (e.g., acrylics), poly($C_1$-$C_6$) acrylates, acrylate copolymers, polyalkyl alkacrylates wherein the alkyl and alk groups independently contain one to six carbon atoms, polyacrylonitrile, polyvinylacetate, cellulose acetate butyrate, nitrocellulose, copolymers of urethane/carbonate, copolymers of styrene/maleic acid, and mixtures thereof. Copolymers of urethane/carbonate include polycarbonates that are diol terminated which are then reacted with a diisocyanate such as methylene bisphenyl diisocyanate to provide for the urethane/carbonate copolymers. Likewise, copolymers of styrene/maleic acid refer to copolymers having a ratio of styrene to maleic acid of from about 7:3 to about 3:7. Preferably, the biocompatible polymer is also non-inflammatory when employed in situ. The particular biocompatible polymer employed is not critical and is selected relative to the viscosity of the resulting polymer solution, the solubility of the biocompatible polymer in the biocompatible solvent, and the like. Such factors are well within the skill of the art.

The polymers of polyacrylonitrile, polyvinylacetate, poly($C_1$-$C_6$) acrylates, acrylate copolymers, polyalkyl alkacrylates wherein the alkyl and alk groups independently contain one to six carbon atoms, cellulose acetate butyrate, nitrocellulose, copolymers of urethane/carbonate, copolymers of styrene/maleic acid and mixtures thereof typically will have a molecular weight of at least about 50,000 and more preferably from about 75,000 to about 300,000.

Preferred biocompatible polymers include cellulose diacetate and ethylene vinyl alcohol copolymer. In one embodiment, the cellulose diacetate has an acetyl content of from about 31 to about 40 weight percent. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the implanting properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 8 weight-volume percent of the ethylene vinyl alcohol copolymer in DMSO has a viscosity equal to or less than 60 centipoise at 20° C. and more preferably 40 centipoise or less at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution. In a particularly preferred embodiment, the copolymers employed herein comprise a mole percent of ethylene of from about 25 to about 60 and a mole percent of vinyl alcohol of from about 40 to about 75, more preferably a mole percent of ethylene of from about 40 to about 60 and a mole percent of vinyl alcohol of from about 40 to about 60.

The term "contrast agent" refers to abiocompatible (non-toxic) radiopaque material capable of being monitored during injection into amammalian subjectby, for example, radiography. The contrast agent can be either water soluble or water insoluble. Examples of water soluble contrast agents include metrizamide, iopamidol, iothalamate sodium, iodomide sodium, and meglumine. The term "water insoluble contrast agent" refers to contrast agents which are insoluble in water (i.e., has a water solubility of less than 0.01 milligrams permilliliter at 20° C.) and include tantalum, tantalum oxide and barium sulfate, each of which is commercially available in the proper form for in vivo use and preferably having a particle size of 10 µm or less. Other water insoluble contrast agents include gold, tungsten and platinum powders. Methods for preparing such water insoluble biocompatible contrast agents having an average particle size of about 10 µm or less are described below. Preferably, the contrast agent is water insoluble (i.e., has a water solubility of less than 0.01 mg/ml at 20° C.)

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, ethyl lactate, acetone, and the like. Aqueous mixtures with the biocompatible solvent can also be employed provided that the amount of water employed is sufficiently small that the dissolved polymer precipitates upon injection into a human body. Preferably, the biocompatible solvent is ethyl lactate or dimethylsulfoxide.

The term "encapsulation" as used relative to the contrast agent being encapsulated in the precipitate is not meant to infer any physical entrapment of the contrast agent within the precipitate much as a capsule encapsulates a medicament. Rather, this term is used to mean that an integral coherent precipitate forms which does not separate into individual components, for example into a copolymer component and a contrast agent component.

The compositions employed in the methods of this invention are prepared by conventional methods whereby each of the components is added and the resulting composition mixed together until the overall composition is substantially homogeneous. For example, sufficient amounts of the selected polymer are added to the biocompatible solvent to achieve the effective concentration for the complete composition. Preferably, the composition will comprise from about 2.5 to about 20.0 weight percent of the polymerbased on the total weight of the composition and more preferably from about 4 to about 12 weight percent. If necessary, gentle heating and stirring can be used to effect dissolution of the polymer into the biocompatible solvent, e.g., 12 hours at 50° C.

Sufficient amounts of the contrast agent are then optionally added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 to about 35 weight percent. When the contrast agent is not soluble in the biocompatible solvent, stirring is employed to effect homogeneity of the resulting suspension. In order to enhance formation of the suspension, the particle size of the contrast agent is preferably maintained at about 10 µm or less and more preferably at from about 1 to about 5 µm (e.g., an average size of about 2 µm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, gamma irradiation, or electron beam induced polymerization employing, as necessary, a polymerization catalyst or polymerization initiator to provide for the polymer composition. The specific manner of polymerization is not critical and the polymerization techniques employed do not form a part of this invention. In order to maintain solubility in the biocompatible solvent, the polymers described herein are preferably not cross-linked.

In another particularly preferred embodiment of the implant-forming or augmenting solution, the biocompatible polymer composition can be replaced with a biocompatible prepolymer composition containing a biocompatible prepolymer. In this embodiment, the composition comprises a biocompatible prepolymer, an optional biocompatible water insoluble contrast agent preferably having an average particle size of about 10 µm or less and, optionally, a biocompatible solvent.

The term "biocompatible prepolymer" refers to materials which polymerize in situ to form a polymer and which, in the amounts employed, are non-toxic, chemically inert, and substantially non-immunogenic when used internally in the patient and which are substantially insoluble in physiologic liquids. Such a composition is introduced into the body as a mixture of reactive chemicals and thereafter forms abiocompatible polymer within the body. Suitable biocompatible prepolymers include, by way of example, cyanoacrylates, hydroxyethyl methacrylate, silicon prepolymers, and the like. The prepolymer can either be a monomer or a reactive oligomer. Preferably, the biocompatible prepolymer is also non-inflammatory when employed in situ.

Prepolymer compositions can be prepared by adding sufficient amounts of the optional contrast agent to the solution (e.g., liquid prepolymer) to achieve the effective concentration for the complete polymer composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 µm or less and more preferably at from about 1 to about 5 µm (e.g., an average size of about 2 µm).

When the prepolymer is liquid (as in the case of polyurethanes), the use of a biocompatible solvent is not absolutely necessary but may be preferred to provide for an appropriate viscosity in the implant-forming solution. Preferably, when employed, the biocompatible solvent will comprise from about 10 to about 50 weight percent of the biocompatible prepolymer composition based on the total weight of the prepolymer composition. When a biocompatible solvent is employed, the prepolymeric composition typically comprises from about 90 to about 50 weight percent of the prepolymer based on the total weight of the composition.

In a particularly preferred embodiment, the prepolymer is cyanoacrylate which is preferably employed in the absence of abiocompatible solvent. When so employed, the cyanoacrylate adhesive is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Other suitable implant-forming materials for introduction into one or both of muscle layers 201 and 202 include injectable bioglass as described in Walker et al., "Injectable Bioglass as a Potential Substitute for Injectable Polytetrafluorethylene Particles", J. Urol., 148:645-7, 1992, small particle species such as Polytetrafluoroethylene (PTFE) particles in glycerine such as Polytef®, biocompatible compositions comprising discrete, polymeric and silicone rubber bodies such as described in U.S. Pat. Nos. 5,007,940, 5,158,573 and 5,116,387 to Berg, biocompatible compositions comprising carbon coated beads such as disclosed in U.S. Pat. No.5,451,406 to Lawin, collagen and other biodegradable material of the type disclosed in U.S. Pat. No. 4,803,075 to Wallace et al. and other known injectable materials.

Specific embodiments of implant-forming solutions suitable for use in the apparatus and methods of the invention are described in U.S. Pat. Nos. 5,667,767 dated Sept. 16, 1997, Pat. No. 5,580,568 dated Dec. 3, 1996 and 5,695,480 dated Dec. 9, 1997 and International Publication Number WO 97/45131 having an International Publication Date of Dec. 4, 1997, the entire contents of which are incorporated herein by this reference.

A suitable supply assembly for depositing one or more implants in the rectal area of the patient is coupled to the proximal extremity of the probe member. The supply assembly includes at least a first reservoir containing the implant-forming material. As noted above, such implant-forming solution preferably includes at least one nonaqueous solution and more preferably is a solution of a biocompatible polymer and a biocompatible solvent. Preferably, the supply assembly further includes a second reservoir containing a solvent and preferably a biocompatible solvent such as dimethyl sulfoxide (DMSO) and a third reservoir containing a suitable aqueous or physiologic solution such as saline.

In the method of the present invention, let it be assumed that in preparing for the procedure, the gastrointestinal tract of a patient has been previously evaluated by using any or all techniques and procedures available in the art including, but not limited to, upper and lower gastrointestinal radiographic studies, motility studies, endoscopy with biopsies, proctoscopy, sigmoidoscopy and colonoscopy. Assuming that the patient's pretreatment evaluation warrants the procedure hereinafter described and that the patient has received a typical surgical bowel preparation as is known in the art, the patient can be brought into an outpatient clinic or an operating room in a hospital. The patient is preferably placed in either a lithotomy or jackknife position on an operating or examining table or on a gurmey.

After intravenous access has been accomplished and the patient has been appropriately sedated or anesthetized, the physician inserts a suitable probe member or scope, for example an anoscope, a proctoscope or a sigmoidoscope, in a standard manner. After appropriate positioning of the scope to identify the appropriate region of the rectal wall 24 for treatment, the scope is removed from the rectum. The physician or his assistant then fills and primes syringe 41, in the manner described in U.S. patent application Ser. No. 09/286,245 filed Apr. 5, 1999, with a saline or other suitable aqueous or physiological solution from the third reservoir of the supply assembly, referred to herein as the saline solution. The distal extremity of needle 43 is introduced through anus 23 of the patient and passed into the region of anal sphincter 31 as seen in FIG. 1. In this regard, the handle of syringe 41 is grasped by the physician in order to introduce the distal extremity of needle 43 into anus 23 and advance it in a cephalad direction to the vicinity of sphincter 31, the area to be treated. By subsequently advancing needle 43 laterally, the physician penetrates wall 24 of anus 23 with the sharpened end of needle 43 which causes the distal end thereof to penetrate anal sphincter 31.

Alternatively, the scope can be maintained in anal canal 23 during the procedure in order to maximize exposure and visibility. In such a case, needle 43 or a catheter-type needle, that is a needle at the end of a catheter, is advanced through the scope and beyond the distal end thereof to the area of treatment instead of being advanced directly through anus 23. It should also be appreciated that the treatment of the present invention can be performed with an appropriately modified biopsy guide in conjunction with a trans-rectal ultrasound system (TRUS).

In one of the embodiments of the invention the saline solution from the third reservoir of the supply assembly can be injected into wall 24 and more specifically into internal sphincter 32. The saline injection creates to a local edema for facilitating acceptance of the implant by the body of the patient. The amount of injected saline solution can range from 0.25 to 10 cc and preferably ranges from 1 to 3 cc. Thereafter, the physician retracts needle 43 from wall 24, removes syringe 41 from anus 23, subsequently withdrawing the remaining saline solution from the needle passage and flushing the needle passage with DMSO from the second reservoir to ensure that the saline solution has been removed from the passage. Removal of the saline solution from the needle passage and the cleansing of the passage with DMSO inhibits premature precipitation within syringe of the biocompatible polymer in the implant-forming solution of the first reservoir from the DMSO in such implant-forming solution. The needle passage is next primed with the implanting-forming solution from the first reservoir.

The physician subsequently causes the distal portion of needle 43 to penetrate the internal sphincter and thereafter causes a preselected amount of the implant-forming solution to be introduced through needle 43. The optional contrast agent within the implant-forming solution permits the viewing of the solution by means of fluoroscopy. In addition, the introduction of the implant-forming solution into wall 24 can be monitored by standard abdominal or pelvic ultrasound or, preferably, by high resolution trans-rectal ultrasound system. The rate of injection of the implant-forming solution into the space can range from 0.1 cc per minute to 10 cc per minute. Once the implant-forming solution has been introduced into wall 24, the biocompatible polymer of the implant-forming solution precipitates to form one or more discrete deposits or solid implants 51 (see FIGS.1-2). The bio-compatible solvent disperses in body 22. The amount of implant-forming solution injected into wall 24 for each implant 51 can range from 0.05 cc to 10 cc.

It has been found that an injection of a suitable aqueous or physiologic solution such as a saline solution into wall 24 prior to the injection of the implant-formning solution serves to condition or prepare the tissue in wall 24, that is to help wall 24 receive the implant-forming solution and thus facilitate implantation of the biocompatible polymer. Although the conditioning solution has been described as a saline solution, antibiotics and/or anti-inflammatories can be introduced locally to condition the tissue. The use of a saline solution as discussed above also facilitates the rapid dispersion of the DMSO from the implant-forming solution thus diluting any local irritant effect of the DMSO. The saline solution further acts as a heat sink for the heat of dissolution of the solvent.

Any number and configuration of implants 51 can be formed in rectal wall 24. In one preferred method, a plurality of circumferentially spaced-apart implants 51 are formed in rectal wall 24 (see FIGS. 1-2). The discrete implants 51 can be formed in submucosal layer 27, circular muscle layer 28 and/or longitudinal muscle layer 29. In addition, the implants 51 can be formed in anal sphincter 31, as shown in FIGS. 1-2 where implants 51 are located in sphincter ani internus 32. It should be appreciated that implants 51 can also be formed in any or all of the portions of sphincter ani internus 32, sphincter ani externus 33, namely, deep external sphincter 34, superficial external sphincter 36 and/or subcutaneous external sphincter 37, and/or in the intersphincteric space 39. An exemplary implant 52 formed by dashed lines is shown in each of deep external sphincter 34, superficial external sphincter 36 and subcutaneous external sphincter 37 in FIG. 1.

When a plurality of implants 51 are formed in rectal wall 24 in the vicinity of anus 23, such implants can be disposed substantially in a plane, as shown in FIGS. 1-2, in multiple planes or out of plane. Implants 51 can be symmetrically or asymmetrically disposed around anus 23. Such implants can be formed from pulsed or continuous injections of a solution from syringe 41 or by any other suitable manual or automated means.

In a particularly preferred embodiment of the present invention one or more elongate implants 53 having respective longitudinal axes 54 are formed in lax internal sphincter 32, as seen in FIG. 3, by using any of the solutions hereinbefore described. In order to perform the method in such a manner, the physician utilizes a longer needle 43, preferably a needle having a length of at least 3.5 to 5.0 inches, under direct vision. Holding syringe 41 as hereinbefore described, the physician advances needle 43 similarly, in a cephalad and then lateral direction into and through internal sphincter 32 until the distal end of needle 43 abuts or approximates anorectal border 38, above internal sphincter 32. Using a pull-back technique of injection, the physician injects and deposits implant-forming solution in the muscle of internal sphincter 32 while slowly withdrawing needle 43, thereby creating an elongate, longitudinally oriented implant 53 therein. Preferably, rod-shaped implants 53 formed in this manner have a length of approximately 20-100 millimeters and a width of approximately 0.1 to 25 millimeters, depending on the dimensions of the sphincter being augmented or treated.

Elongate implants 53 preferably extend from the cephalad to caudal ends of internal sphincter 32 or from anorectal border 38 to opening of anus 23. As such, the longitudinal axis of 54 each of the implants 53 extends substantially parallel to the centerline of the rectum. It should be appreciated that with this technique, while a single elongate implant 53 can be deposited at any location within internal sphincter 32, a greater number of implants can be spaced apart therein. Preferably, at least four such implants are placed circumferentially, at approximately ninety degrees of separation from one another, within internal anal sphincter 32. Each quadrant of internal sphincter 32 is thereby enlisted to participate substantially equally in augmenting sphincter competency. In this manner elongate implants 53 bolster, stiffen and increase the tonus of an otherwise lax internal sphincter 32, helping to maintain and restore the anatomical configuration and function thereof. As hereinbefore described, diminished distensibility of internal sphincter 32 ameliorates anal incontinence.

In another preferred embodiment, similarrod-like implants 53 are formed within a disrupted internal sphincter 32 in order to restore the structural and functional integrity thereof as seen in FIG. 4. The apparatus and technique of forming implants 53 are as hereinbefore described. Any of the materials discussed above for creating implants in a body can be utilized. However, the implants are preferably formed from an injectable solution of a biocompatible polymer and a biocompatible solvent from which the biocompatible polymer precipitates when the solution is introduced into the body. Inasmuch as the size and distribution of an implant created depends in part upon the quantity of implant-forming material, speed of injection thereof and the space or tissue into which the material is injected, the technique of pull-back injection utilized with this embodiment is performed particularly slowly in order to form an elongate implant 53 which bridges the damaged or incompetent portion 60 of internal sphincter 32. Specifically, needle 43 is extended up through the second end portion 59, the damaged portion 60 and then the first end 58, before being slowly pulled back during delivery of the implant-forming material into the sphincter 32. By bracing the damaged internal sphincter 32, function is restored and end portions 58 and 59 can again properly function together as a unit.

The elongate implants of the present invention can be formed in any other portion of the wall of the gastrointestinal tract, or in any other wall forming apassageway in a body of a mammal. In addition, the technique disclosed above for bracing or restoring a muscle, for example a muscle having a damaged or incompetent portion, can be utilized elsewhere in a body of a mammal. It should further be appreciated that arc-shaped, arcuate and/or ring-shaped implants, for example of the type disclosed in U.S. patent application Ser. No. 09/447,663 filed Nov. 23, 1999, the entire content of which can be incorporated herein by this reference, can also be formed in any of the muscle layers of the rectal wall 24.

Figure 5:
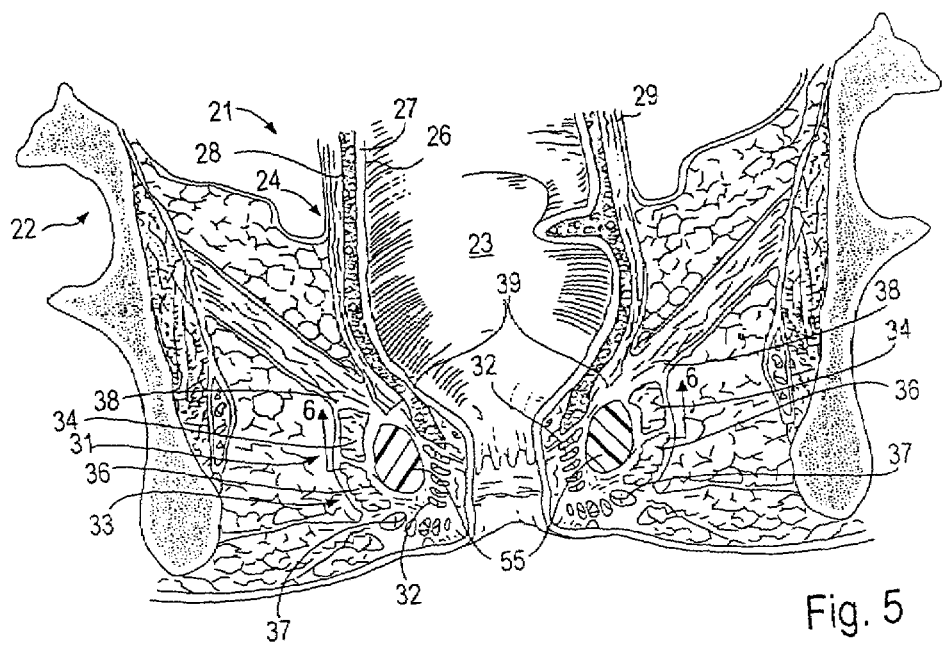
FIG. 5 is a sectional view of a portion of the human body similar to FIG. 1 in which a portion of the anal sphincter is being treated by yet another method of the present invention.
Figure 6:
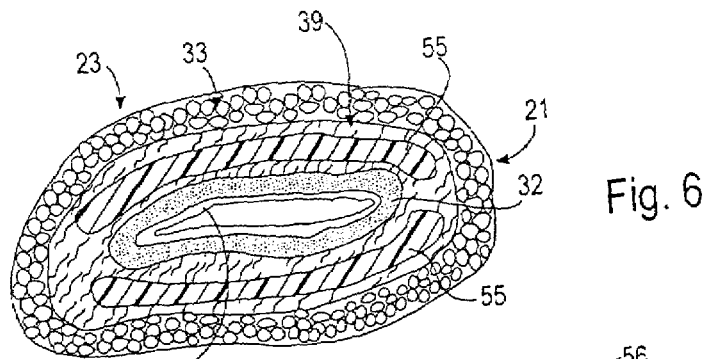
FIG. 6 is a cross-sectional view taken along the line 6-6 of FIG. 5.

In another particularly preferred embodiment of the present invention, one or more implants 55 are formed in intersphincteric space 39, as seen in FIGS. 5-6, either exclusively or in conjunction with internal sphincter implants 51 hereinbefore described. Techniques and apparatus are as hereinbefore described. The implants are preferably formed from an injectable solution of a biocompatible polymer and a biocompatible solvent from which the biocompatible polymer precipitates when the solution is introduced into the body. In addition, intersphincteric space 39 is located using pelvic ultrasound or, preferably, high resolution trans-rectal ultrasound. Preferably, intersphincteric implants 55 are circumferentially spaced apart and arcuate or ring-like in configuration. In comparison to external or internal sphincters 33 and 32, intersphincteric space 39 is substantially without striations, septa or fibrous bands and, as such, is more capacious. Therefore, a fully circumferential ring-like implant can be much more easily formed therein, for example by ejecting material laterally or horizontally out of side openings of needle 43. A circumferential intersphincteric implant 55 facilitates augmentation of a lax anal sphincter 31. To this end, preferably, the physician uses a needle 43 provided with a plurality of longitudinally and spaced-apart openings. In order to create a plurality of implants, multiple separate injections in intersphincteric space 39 are performed. Two arcuate implants are shown in FIGS. 5 and 6. A ring-shaped implant can be formed by forming a plurality of arcuate implants which abut each other to form the ring-shaped implant.

The optional contrast agent in the implants permits the implants to be monitored after completion of the procedure described above. Thus the stability of the implants and their configurations can be observed over time. Further procedures can be performed to supplement previously formed implants. It should be appreciated that the implants of the present invention can be used as delivery vehicles for other materials such as radio-isotopes, chemotherapeutic agents, anti-inflammatory agents and/or antibiotics.

The treatment of the invention can be reversed by expanding the augmented or coapted region created by the implants in an suitable manner such as by use of a balloon or bougie.

Although the method of the invention has been described as including the injection of a saline solution into the wall 24 prior to an injection of implant-forming solution into the wall 24, it should be appreciated that the implant-forming solution can be injected into wall 24 without such a prior injection of saline or other solution. A saline or other aqueous or physiologic solution can optionally be introduced into the wall 24 after the introduction of the implant-forrr ng solution therein to facilitate dispersion of the DMSO or other biocompatible solvent present in the implant-forming solution. It can thus be seen that the invention is broad enough to cover the introduction of any conditioning solution into the tissue after the treatment to facilitate the treatment.

Although in the described method of the invention the delivery needle has been introduced through the rectal wall, formation or placement of implants in or about the anal sphincter can be accomplished transperineally and be within the scope of the present invention. In this regard, one or more needles for delivery of the implant-forming material can be introduced through the perineum for accessing the anal sphincter, the intersphincteric space 39 and/or other tissue in the vicinity thereof. Such implant formation can be visualized and monitored under ultrasound or any other conventional means. As such, introduction into the rectal wall can be accomplished from the rectal cavity or through the perineum.

It should be appreciated that additional configurations and types of needles are included within the purview of the present invention. Thus, needles provided with any combination of longitudinally and/or circumferentially spaced-apart side openings can be used to facilitate the formation of arcuate, thicker and/or wider implants. In addition to needles carrying cutting tips, needles provided with blunt tips may be utilized.

Figure 7:
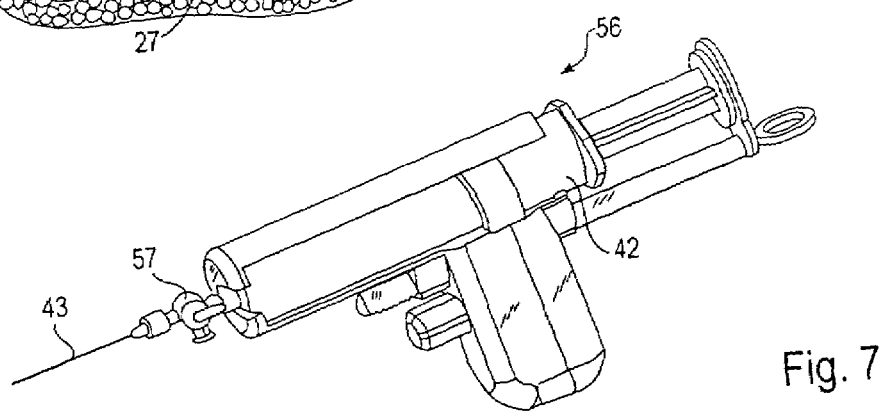
FIG. 7 is a perspective view of an apparatus for use in the method for treating the anal sphincter of the present invention.

It should also be appreciated that other apparatus can be utilized to augment, bulk or otherwise decrease the distensibility of rectal wall 24 in the vicinity of anus 23. For example, as shown in FIG. 7, a delivery mechanism or gun 56 which provides preselected amounts of the solution into rectal wall 24 can be utilized. Gun 56 is substantially similar to the gun shown in U.S. patent application No. Ser. No. 09/286,245 filed Apr. 5, 1999. Syringe 41 can be utilized with gun 56 and a stop cock 57 can be disposed between syringe 41 and needle 43 for permitting a biocompatible solvent such as DMSO and/or an aqueous solution such as saline to be alternatively introduced through needle 43 into rectal wall 24. Reservoirs such as additional syringes (not shown) can be utilized in this regard.

It can be seen from the foregoing that the implants formed by the method of the present invention can be of a variety of sizes and formed in a variety of configurations in the wall of the rectum and anal canal. Anymaterial or solution utilized for forming such implants can be injected into the wall in a variety of manual or automated and pulsed on continuous manners. One or more implants can be formed in any of the layers of the wall, including any of the muscle layers or inter-muscular layers of the wall. Without limiting the foregoing, it should be appreciated that any of the implants of the invention hereinbefore described can be formed in any sphincter-like muscle or mechanism in the gastrointestinal tract or elsewhere in the body.

What is claimed is:

1. A method for treating fecal incontinence in a body of a mammal having a rectum formed by a rectal wall extending to an anus wherein the rectal wall includes a sphincter muscle surrounding the anus comprising the steps of introducing a biocompatible prepolymer into the rectal wall in the vicinity of the anus and polymerizing the biocompatible prepolymer in situ to form a nonbiodegradable solid in the rectal wall.

2. The method of claim 1 wherein the polymerizing step includes the step of forming a plurality of discrete nonbiodegradable solids in the rectal wall around the anus.

3. The method of claim 2 wherein said polymerizing step includes forming a plurality of rod-shaped solids.

4. The method of claim 1 wherein the rectal wall includes an intersphincteric space and wherein the polymerizing step includes the step of forming said solid in the intersphincteric space.

5. The method of claim 1 wherein the rectal wall includes an anorectal border and wherein the polymerizing step includes forming at least one solid extending from the anorectal border to the anus.

6. The method of claim 1 wherein the introducing step includes the step of introducing the biocompatible prepolymer into the sphincter muscle.

7. The method of claim 6 wherein the sphincter muscle includes a sphincter ani internus and wherein the introducing step includes the step of introducing the biocompatible prepolymer into the sphincter ani internus.

8. The method of claim 6, wherein the sphincter muscle includes a sphincter ani externus and wherein the introducing step includes the step of introducing the biocompatible prepolymer into the sphincter ani externus.

9. The method of claim 1 wherein the biocompatible polymer is part of a composition having a contrast agent for facilitating visualization of the nonbiodegradable solid in the rectal wall.

10. The method of claim 1 wherein the introducing step includes the steps of extending a needle into the rectal wall and supplying the biocompatible polymer through the needle into the rectal wall.

11. The method of claim 10 wherein the extending step includes the step of extending the needle from the rectal cavity into the rectal wall.

12. The method of claim 10 wherein the extending step includes the step of extending the needle through the perineum into the rectal wall.

13. The method of claim 1 wherein the biocompatible prepolymer is part of a composition having a biocompatible solvent.

14. A method for treating fecal incontinence in a body having an anal sphincter comprising the step of polymerizing a biocompatible prepolymer in situ to form at least one nonbiodegradable implant in said sphincter.

15. The method of claim 14 further including the step of introducing a biocompatible prepolymer into said sphincter.

16. The method of claim 15 wherein the introducing step includes the steps of introducing a needle into the sphincter and introducing the biocompatible prepolymer through the needle into the sphincter.

17. The method of claim 14 wherein said sphincter has a damaged portion, further including the step of bridging the damaged portion with the implant.

18. The method of claim 14 wherein the anal sphincter has an internal sphincter and wherein the polymerizing step includes the step of forming the at least one implant in said internal sphincter.

* * * * *